US012653971B2

(12) United States Patent
Alizoti et al.

(10) Patent No.: US 12,653,971 B2
(45) Date of Patent: Jun. 16, 2026

(54) MEDICAL DEVICE WITH ENERGY HARVESTING SYSTEM

(71) Applicant: Trudell Medical International Inc., London (CA)

(72) Inventors: Neritan Alizoti, London (CA); Sam Bender, Thornhill (CA); Adam Meyer, London (CA); Geoffrey Nielsen, London (CA); Bart Nowak, London (CA); Peter Scarrott, London (CA)

(73) Assignee: Trudell Medical International Inc., London (CA)

( * ) Notice: Subject to any disclaimer, the term of this patent is extended or adjusted under 35 U.S.C. 154(b) by 0 days.

(21) Appl. No.: 18/422,464

(22) Filed: Jan. 25, 2024

(65) Prior Publication Data

US 2024/0238539 A1 Jul. 18, 2024

Related U.S. Application Data

(63) Continuation of application No. 17/010,534, filed on Sep. 2, 2020, now Pat. No. 11,911,558.

(Continued)

(51) Int. Cl.
  *A61M 15/00* (2006.01)
  *F03G 5/06* (2006.01)
(52) U.S. Cl.
  CPC ...... *A61M 15/009* (2013.01); *A61M 15/0008* (2014.02); *A61M 15/002* (2014.02); *A61M 15/0021* (2014.02); *A61M 15/0086* (2013.01); *F03G 5/065* (2021.08); *A61M 2205/3331* (2013.01); *A61M 2205/3368* (2013.01);

(Continued)

(58) Field of Classification Search
  CPC ............ A61M 15/002; A61M 15/0008; A61M 15/0021; A61M 15/0086; A61M 2205/3331; A61M 2205/3368; A61M 2205/3673; A61M 2205/502; A61M 2205/8206; A61M 2206/16; A61M 2206/20; A61M 2205/07; A61M 11/02; A61M 15/007; A61M 16/0006; A61M 15/0015; A61M 15/0018; A61M 2205/0294; A61M 2205/825; A61M 2205/8256; A61M 2205/8293; A61M 16/049; A61M 15/009; F03G 5/065;

(Continued)

(56) References Cited

U.S. PATENT DOCUMENTS

| | | | |
|---|---|---|---|
| 5,522,380 A | 6/1996 | Dwork | |
| 6,719,011 B2 | 4/2004 | Cull et al. | |

(Continued)

FOREIGN PATENT DOCUMENTS

| | | |
|---|---|---|
| CA | 2808836 A1 | 3/2012 |
| CA | 2980260 A1 | 9/2016 |

(Continued)

*Primary Examiner* — Elliot S Ruddie
(74) *Attorney, Agent, or Firm* — Crowell & Moring LLP

(57) ABSTRACT

A medical device includes a user interface component and an energy harvesting system coupled to the user interface component. The energy harvesting system energy includes a harvesting component, a power storage device connected to the energy harvesting component and an output is coupled to the user interface and operably connected to the power storage device. A method of using the medical device is also provided.

20 Claims, 18 Drawing Sheets

Related U.S. Application Data

(60) Provisional application No. 62/895,316, filed on Sep. 3, 2019.

(52) U.S. Cl.
CPC ............... *A61M 2205/3673* (2013.01); *A61M 2205/502* (2013.01); *A61M 2205/8206* (2013.01); *A61M 2206/16* (2013.01); *A61M 2206/20* (2013.01)

(58) Field of Classification Search
CPC .... H02J 7/1415; H02J 2310/23; H02K 7/065; H02K 35/00–06; H02K 7/1869–1892
See application file for complete search history.

(56) References Cited

U.S. PATENT DOCUMENTS

| | | | |
|---|---|---|---|
| 7,985,254 | B2 | 7/2011 | Tolkowsky |
| 8,499,758 | B2 | 8/2013 | Bhowmick et al. |
| 9,084,859 | B2 | 7/2015 | Connor |
| 10,314,975 | B2 | 6/2019 | Pfrang |
| 2004/0039295 | A1 | 2/2004 | Olbrich et al. |
| 2007/0017506 | A1* | 1/2007 | Bell .................... A61M 15/009 128/200.23 |
| 2009/0200983 | A1* | 8/2009 | Dyer ...................... H02K 35/02 320/107 |
| 2011/0152707 | A1 | 6/2011 | Jang |
| 2012/0234323 | A1 | 9/2012 | Connor |
| 2013/0020806 | A1 | 1/2013 | Hsu |
| 2013/0053719 | A1 | 2/2013 | Wekell |
| 2013/0324788 | A1 | 12/2013 | Holley et al. |
| 2014/0131388 | A1* | 5/2014 | Heisel ................. A61M 15/009 222/162 |
| 2017/0007169 | A1 | 1/2017 | Dieffenderfer et al. |
| 2017/0333645 | A1* | 11/2017 | Alizoti ............. A61M 15/0086 |
| 2018/0008790 | A1 | 1/2018 | Costella |
| 2019/0015608 | A1 | 1/2019 | Glusker et al. |

FOREIGN PATENT DOCUMENTS

| | | |
|---|---|---|
| EP | 0705614 B1 | 9/2002 |
| EP | 2039930 B1 | 11/2016 |
| EP | 3035987 B1 | 11/2018 |
| JP | 2011025038 A | 2/2011 |
| TW | 482689 B | 4/2002 |
| WO | WO 2015/117046 A1 | 8/2015 |
| WO | WO2018048786 A1 | 3/2018 |

* cited by examiner

FIG. 2A
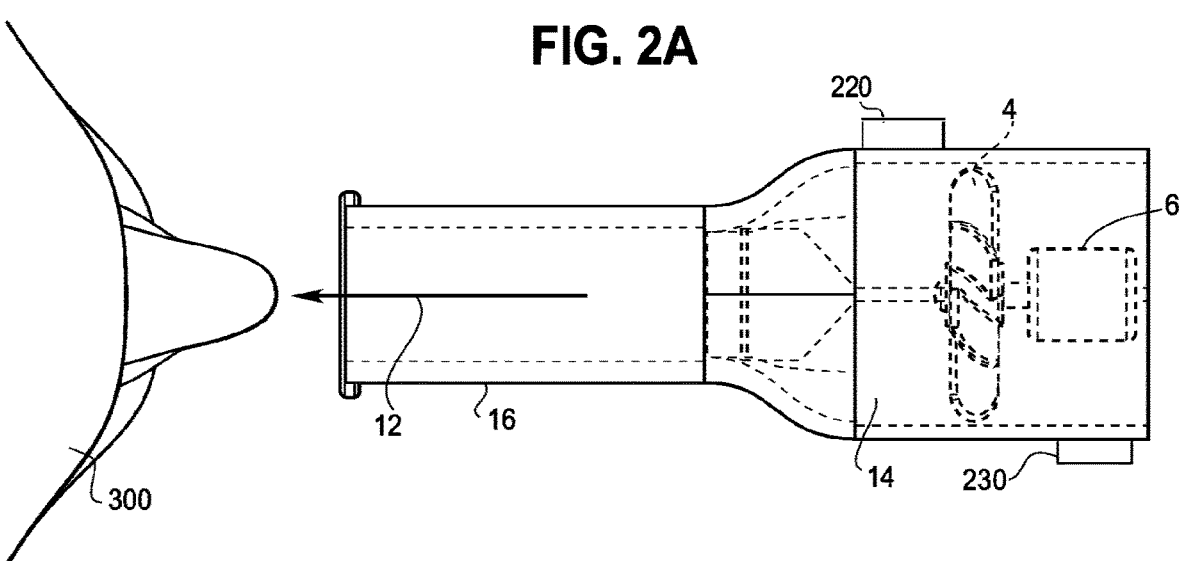
FIG. 2B
FIG. 2C
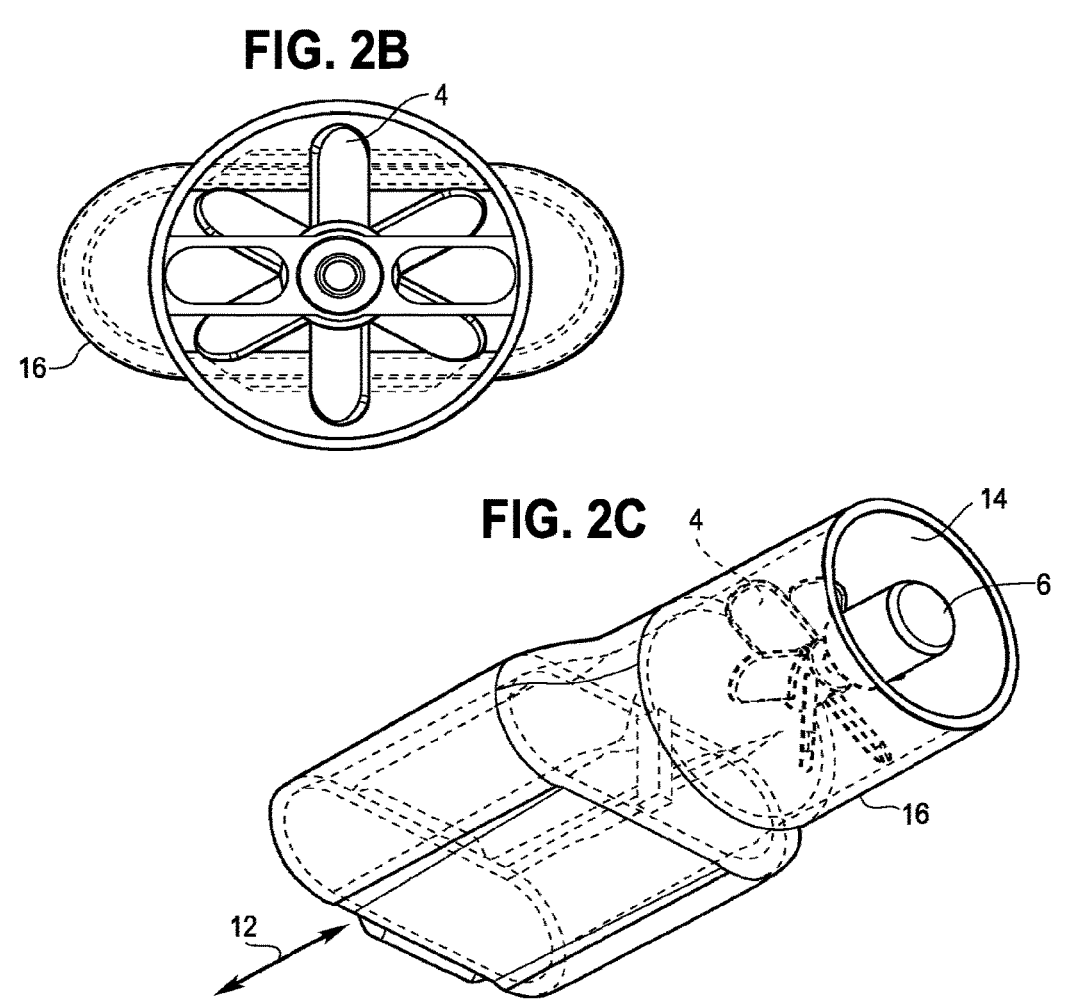

230,220

4          6

34

2     4        6          230,220

4

6

230,220

70

70

220, 230

72

74

72     74

72     74

2     50

MEDICAL DEVICE WITH ENERGY HARVESTING SYSTEM

This application is a continuation of U.S. application Ser. No. 17/010,534, entitled "Medical Device With An Energy Harvesting System," filed Sep. 2, 2020, which claims the benefit of U.S. Provisional Application No. 62/895,316, also entitled "Medical Device With An Energy Harvesting System," and filed Sep. 3, 2019.

TECHNICAL FIELD

A medical device with an energy harvesting system.

BACKGROUND

Medical devices have evolved to include various user feedback features and components that may convey information to a user, care provider, insurance provider and/or others. Such medical devices may include a controller, sensors, communication protocol (e.g., blue tooth), and/or indicators (e.g., display screen, lights or audible/vibratory indicators) requiring a power source. The power source must be periodically charged or replaced to maintain the proper operation of the device.

SUMMARY

In one aspect, one embodiment of a medical device includes a user interface component and an energy harvesting system coupled to the user interface component. The energy harvesting system includes an energy harvesting component operable to generate electrical energy in response to interfacing with the user interface component, and a power storage device connected to the energy harvester component and operable to store the electrical energy received from the energy harvester component. An output is coupled to the user interface and is operably connected to the power storage device.

In another aspect, one embodiment of a method of using a medical device includes interfacing with a user interface component and harvesting energy coupled to the user interface component. The step of harvesting the energy includes generating electrical energy in response to the user interfacing with the user interface component, and storing the electrical energy in a power storage device connected to the energy harvester component. The method further includes providing electrical energy from the power storage device to an output coupled to the user interface.

The present embodiments, together with further objects and advantages, will be best understood by reference to the following detailed description taken in conjunction with the accompanying drawings.

BRIEF DESCRIPTION OF THE DRAWINGS

FIGS. 2A-C show perspective, side and end views of an OPEP configured with an exhalation energy harvester device and system.

DETAILED DESCRIPTION OF THE PRESENTLY PREFERRED EMBODIMENTS

It should be understood that the term "plurality," as used herein, means two or more. The term "coupled" means connected to or engaged with, whether directly or indirectly, for example with an intervening member, and does not require the engagement to be fixed or permanent, although it may be fixed or permanent. It should be understood that the use of numerical terms "first," "second," "third," etc., as used herein does not refer to any particular sequence or order of components. It should be understood that the term "user" and "patient" as used herein refers to any user, including pediatric, adolescent or adult humans, and/or animals.

The term "smart" refers to features that follow the general format of having an input, where information is entered into the system, analysis, where the system acts on or modifies the information, and an output, wherein new information leaves the system. "OPEP" refers to an oscillating positive expiratory pressure device. "VHC" refers to a valved holding chamber. "MDI" refers to a metered dose inhaler. A dose counter 92 may be associated with and connected to the MDI, for example at a top of a medicament container (top mounted), wherein actuation of the dose counter also actuates the MDI, or the dose counter may be integrated into the MDI actuator or boot. Dose counters may also be associated with other medical devices, including dry powder inhalers and pill dispensers.

Propeller Energy Harvesting

Figure 1A:
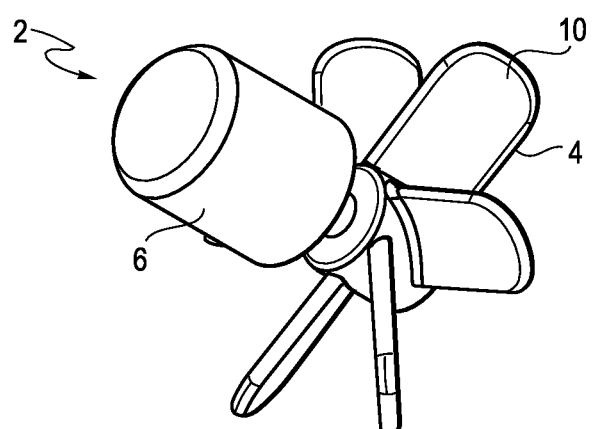
FIGS. 1A-C show perspective, side and end views of a propeller energy harvester device and system.
Figure 1B:
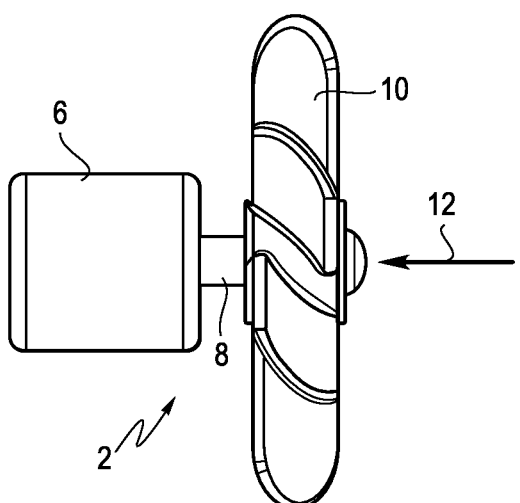
Figure 1C:
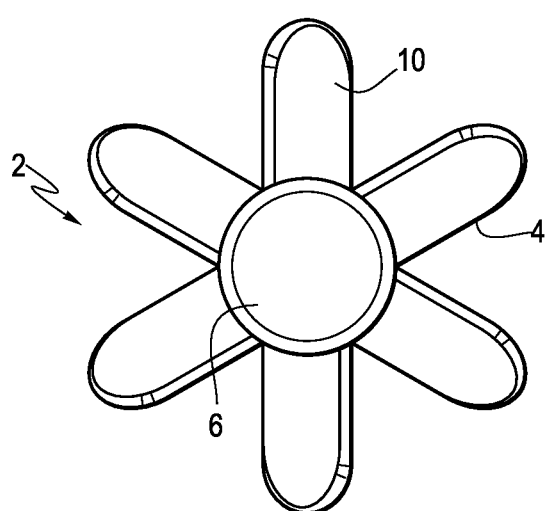

Referring to FIG. 1, an energy harvesting system 2 includes various components, include a propeller 4 that harvests energy from the user's breath. In one embodiment, the propeller 4 is configured with a plurality of blades 10, shown as six, although it should be understood that it may include more or less blades, Airflow can be moving in either direction relative to the propeller to drive movement, for example normal to the propeller along a longitudinal axis 12. The airflow may be created, for example by inhalation and/or exhalation by the user.

Another system component is configured as a generator 6, e.g., a rotary generator, which may be configured as a small brushed DC motor. The generator may be operably connected to the propeller 4 via a shaft 8. The generator may include in one embodiment "DCX 6 M Ø6 mm, precious metal brushes" from Maxon, which provides a power rating of 0.3 W. Similarly, a 0.5w "DCX 8 M Ø8 mm, precious metal brushes" motor may also be used.

Energy from OPEP Exhaled Breath

Referring to FIGS. 2A-C, an energy harvesting system or device is shown as using the user's exhaled breath to generate electrical energy.

The energy harvesting device includes a propeller 4 that drives the generator 6 inside of a cavity 14 of a user interface component 16 of a medical device, with the user interface shown as a mouthpiece and/or adapter of an oscillating positive expiratory pressure device. It should be understood that a similar user interface may be incorporated into other medical devices. In one embodiment, the cavity 14 is 10 mm in diameter. When the user exhales air into the device, or creates air flow in the longitudinal direction 12, the airflow rotates the propeller 4. This rotation drives the generator 6 via the shaft 8, which generates electrical energy that may be stored in an energy storage component, such as a battery 230. The available potential energy may be up to 8 mW.

Integrating a generator 6 into the user interface 16, e.g. mouthpiece of an OPEP device may reduce or eliminate how often the user would have to charge their device. It also may provide feedback information on how the patient is using the device.

Energy from VHC Inhaled Breath

Figure 3A:
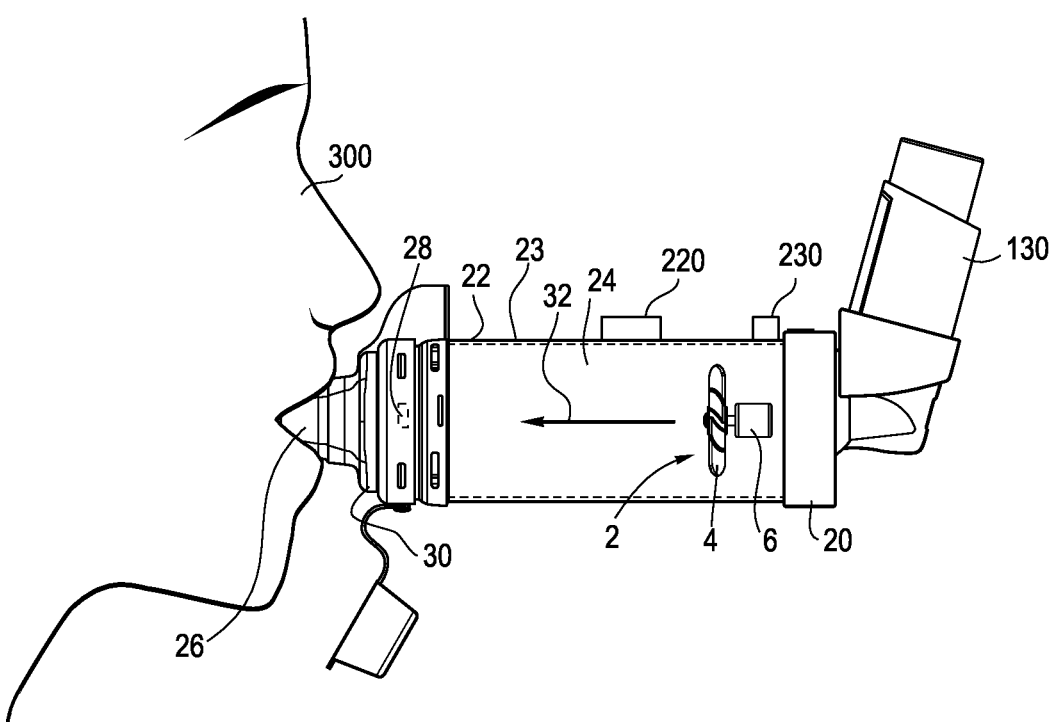
FIGS. 3A and B are sides views of alternative embodiments of a VHC inhalation energy harvester device and system.

Referring to FIGS. 3A and B and 4A-C, an energy harvesting system converts the energy from a user's/patient's inhaled breath, during inhalation, into electrical energy.

Figure 3B:
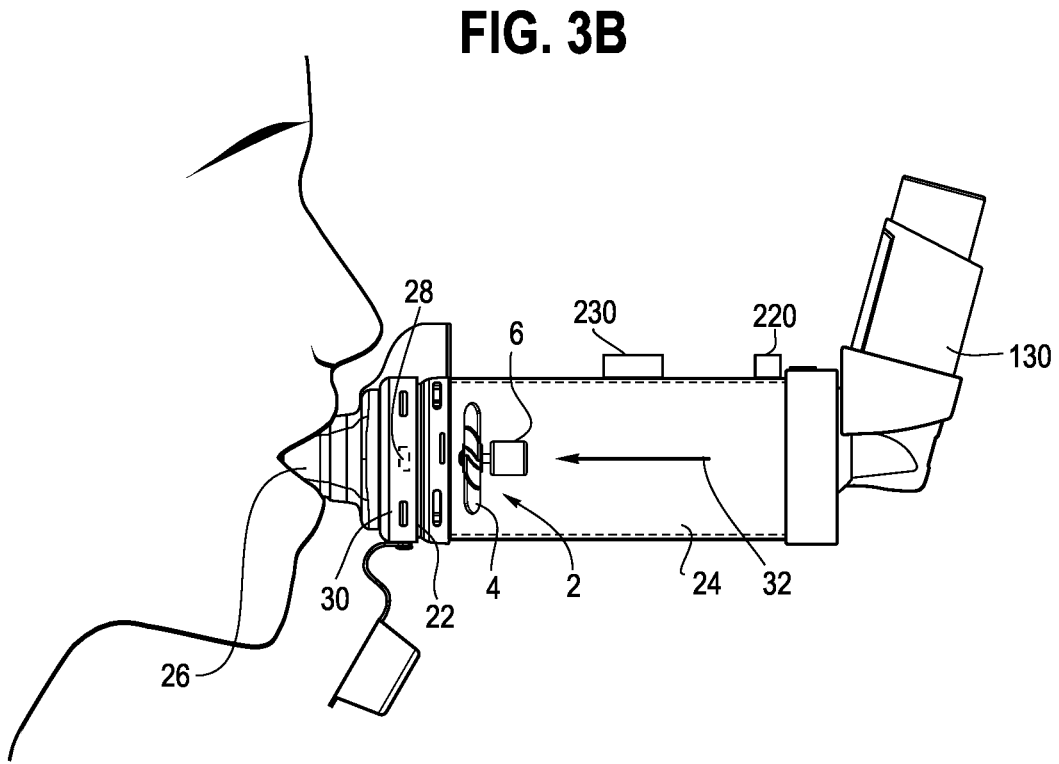

Again, the energy harvesting system includes a generator 6 operable attached/connected to a propeller 4 that is driven when the patient inhales, as opposed to exhales, and creates an airflow path 32. The generator 6 generates energy that may be stored in a battery 230. The system is disposed inside an interior cavity 24 of a medical device, shown as a valved holding chamber 23 having an input end 20 and an output end 22. A medication delivery device 130, such as a metered dose inhaler (MDI) 103 interfaces with the input end, for example by inserting a mouthpiece of an actuator boot into an opening formed in the input end. The harvesting system may be located anywhere inside the interior cavity 24, for example adjacent or closer to the input end 20 (FIG. 3A), or adjacent or closer to the output end 22 (FIG. 3B). Potential energy available may be up to 8 mW. A user interface 26, shown as a mouthpiece, is coupled to the output end 22. The output end and/or user interface may include a one-way inhalation valve 28, and/or one-way exhalation valve 30.

Figure 4A:
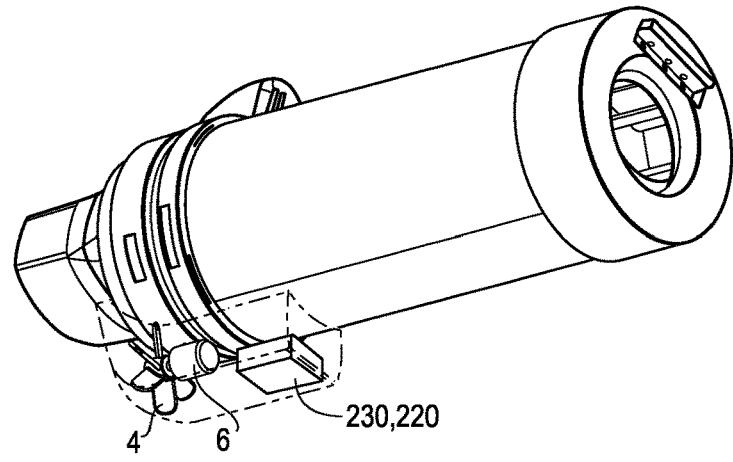
FIGS. 4A-C show perspective, side and end views of a VHC exhalation energy harvester device and system.
Figure 4B:
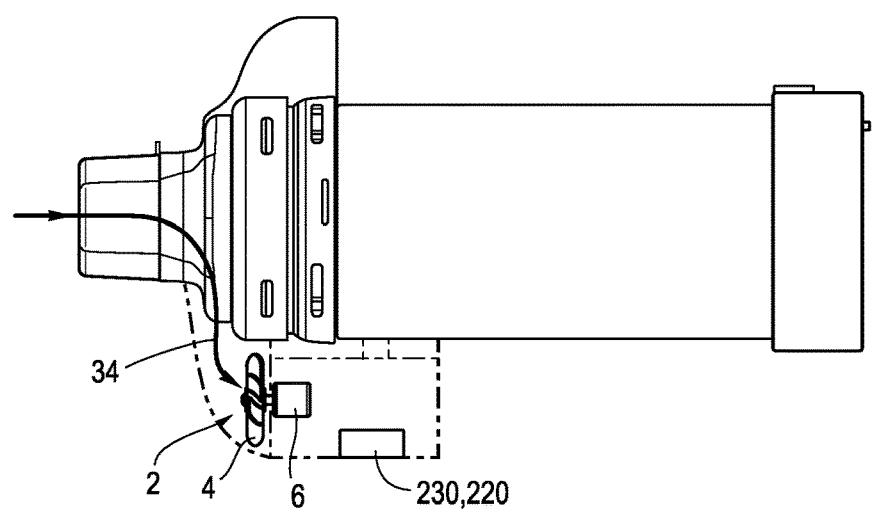
Figure 4C:
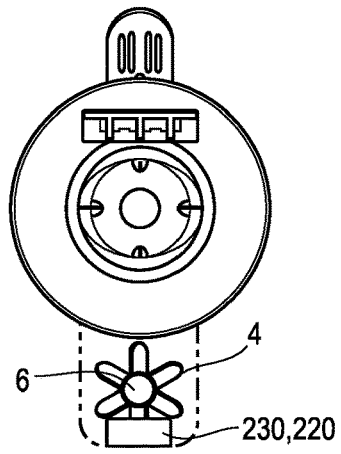
Figures 5A, 5B, 5C:
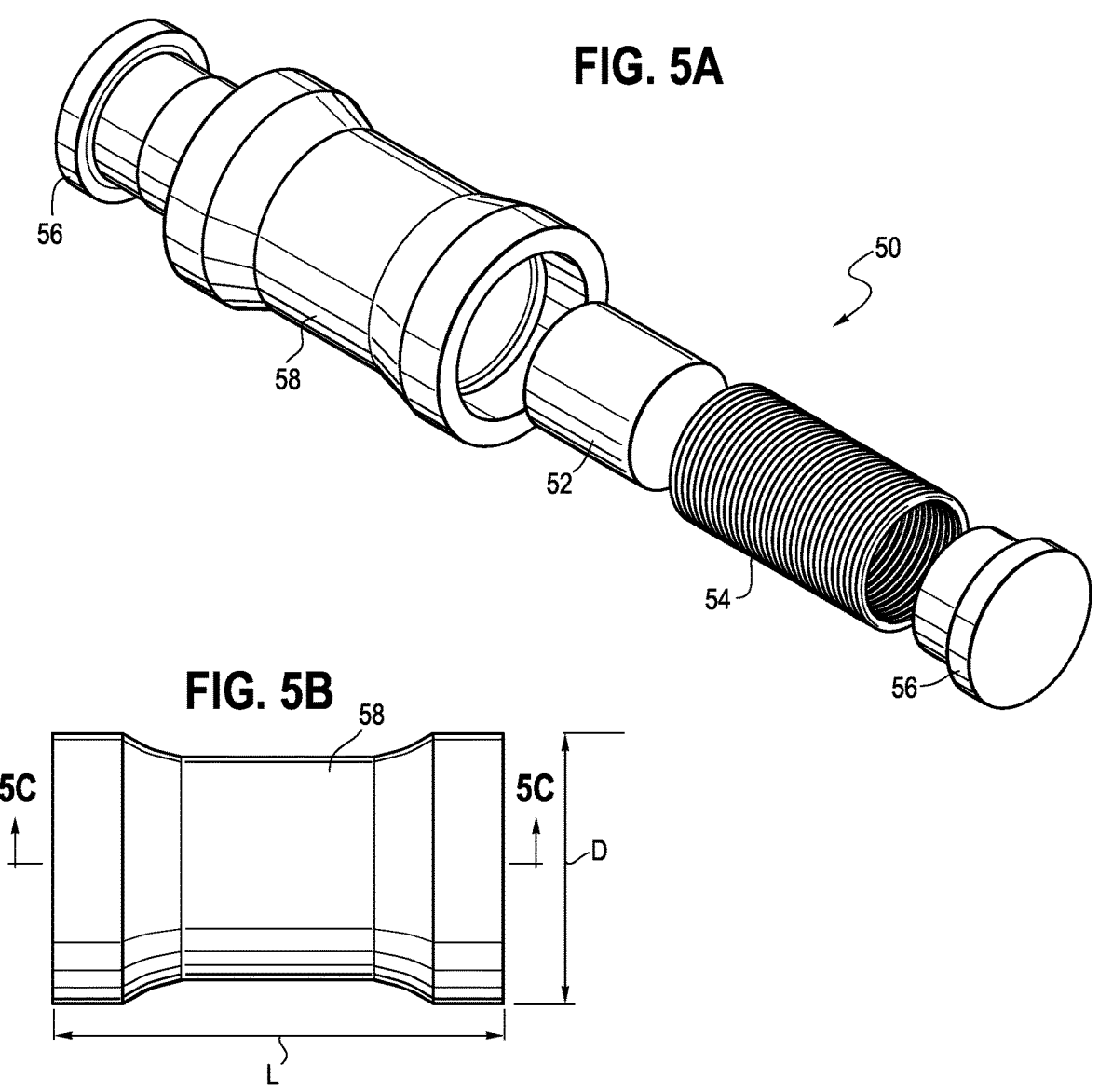
FIGS. 5A-C show an exploded perspective, side and cross-sectional views of a linear generator pressure differential energy harvester device and system.

Alternatively, as shown in FIGS. 4A-C, the energy harvester system includes a generator 6 attached/connected to a propeller 4 that is driven when the patient exhales, or created air flow along an exhalation airflow path 34, for example through the one-way exhalation valve 30 along a bottom of the holding chamber. The harvesting system may be disposed in a housing, having for example a dimension of between 10 mm and 20 mm. The generator generates energy stored in an energy storage device, such as a battery 230. Potential energy available may be up to 8 mW.

Integrating a generator into the body of a VHC may reduce or eliminate how often the user would have to charge their device. It may also provide feedback information on how the patient is using the device.

Pressure Differential Energy Harvesting

Figure 6A:
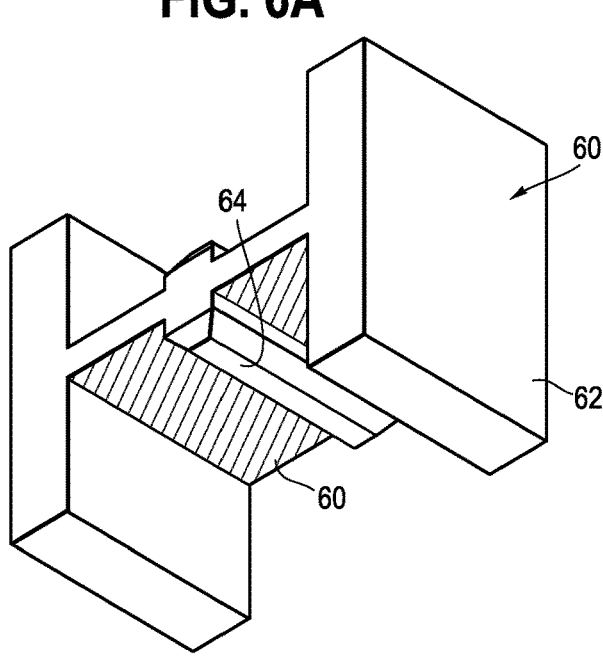
FIGS. 6A-C show perspective, side and end views of a piezo pressure differential energy harvester device and system.
Figure 6B:
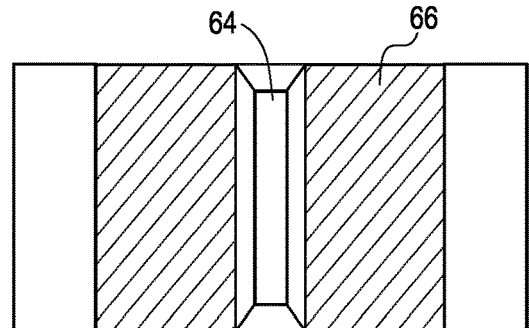
Figure 6C:
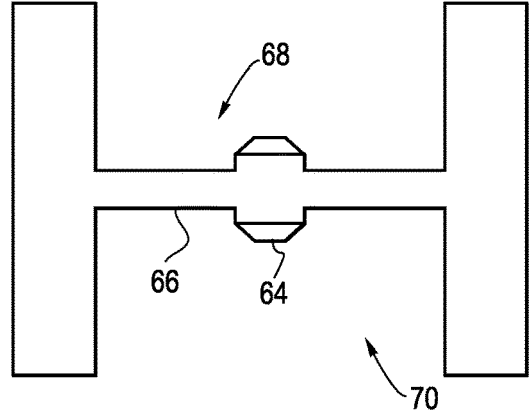

Referring to FIGS. 5A-C and 6A-C, various energy harvesting systems that convert oscillating pressures into electrical energy are shown. The systems may include components such as a linear generator 40 (FIGS. 5A_C) or a piezo element (FIGS. 6A-C).

In one embodiment, shown in FIGS. 5A-C and 7C, an energy harvesting system component includes a linear generator 50 configured with a magnet 52 disposed inside a conductive coil 54. A pair of spaced apart end caps 56(1) push the magnet 52 back and forth relative to the coil 54 when the pressure differential between them changes. The components, including the magnet 52, coil 54, and end caps are enclosed or captured by a housing or enclosure 58. The width or diameter (D) of the housing is between 5 mm and 10 mm, while the overall length (L) of the housing is between 10 and 15 mm. In one embodiment, a neodymium magnet such as "5862K101" from McMaster-Carr may be used. The generator generates energy stored in an energy storage device, such as a battery 230.

Referring to FIGS. 6A-C, an energy harvesting system 60 includes a piezo generator component 62 including a mass 64 that sits in the middle of, or between, two piezo elements 66. When the pressure differential oscillates between opposite sides 68, 70 of the element, the mass 64 vibrates back and forth generating electrical energy.

OPEP Pressure Differential Energy Harvesting

Figures 7A, 7B, 7C:
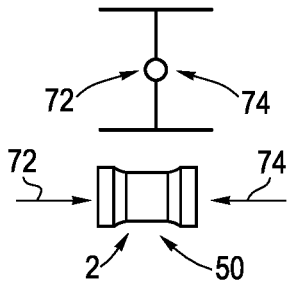
FIGS. 7A and B show a side and cross-sectional view of an OPEP pressure differential energy harvester device and system respectively.
FIG. 7C shows a liner generator pressure differential energy harvester device and system.

Referring to FIGS. 7A-C, an energy harvesting system harvests or transforms energy from oscillating pressures created by a user, for example using a medical device such an OPEP 70.

The OPEP device 70 includes two cavities 72, 74 at different pressures. An energy harvesting system or device 50, 60 may be located or disposed between the two cavities. When the pressure between the two cavities 72, 74 changes, or creates a pressure differential, the energy harvester system 50, 60 generate usable electrical energy. Potential energy available may be up to 4 mW.

The energy harvester device or system is incorporated into an OPEP device 70 to generate electricity through the oscillating pressures. The generator generates energy stored in an energy storage device, such as a battery 230. The generator reduces and/or eliminates how often the user may have to charge their device. It also provides feedback information on how the patient is using the device.

Shaking Energy Harvesting

Figures 8A, 8B, 8C:
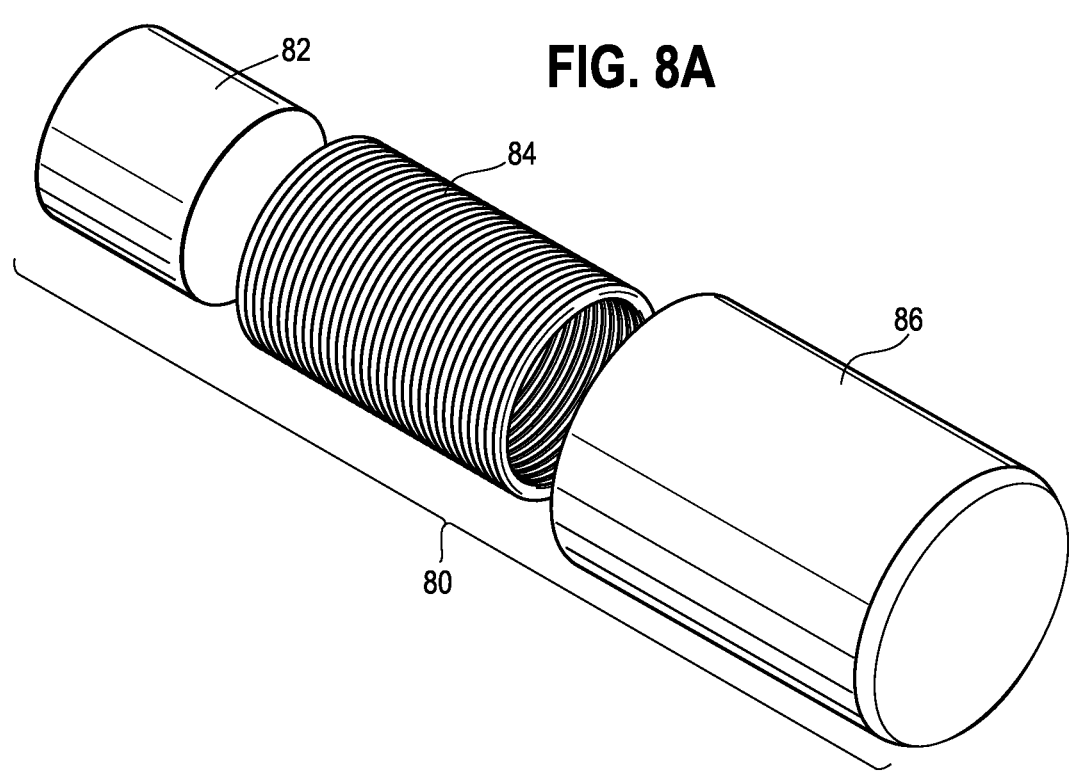
FIGS. 8A-C show exploded perspective, end and cross-sectional views of a shaking linear generator energy harvester device and system.

Referring to FIGS. 8A-C, an energy harvesting device 80 or system transforms the kinetic energy of a magnet 82 into electrical energy is shown. When the magnet 82 moves relative to the conductive coil 84 a current is produced. When the device is shaken the magnet 82 shifts back and forth in the housing 86, configured as a cylindrical case with an interior cavity 88 that receives the magnet and coil.

5

VHC Shaking

Figure 9A:
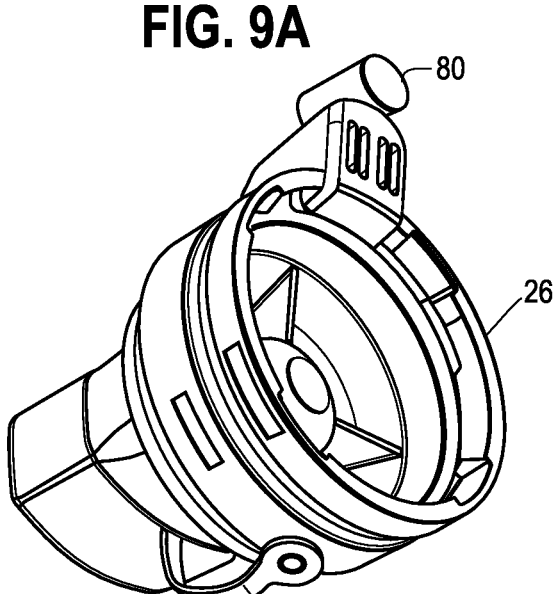
FIGS. 9A-C show perspective, side and end view of a VHC having a shaking energy harvester device and system.
Figure 9B:
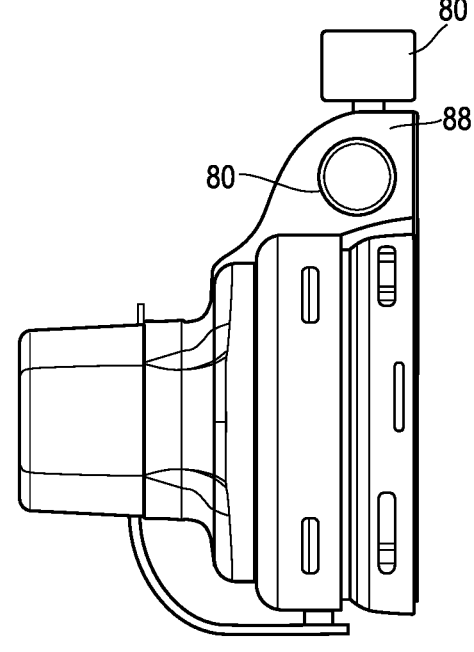
Figure 9C:
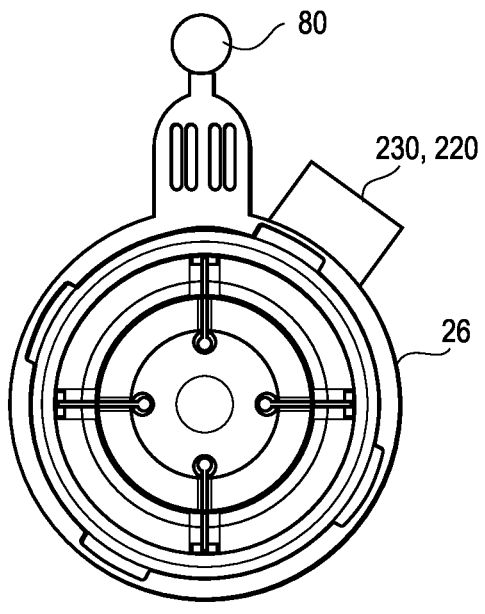

Referring to FIGS. 9A-C the energy harvesting device 80 is coupled to a VHC, for example the top of the user interface 26, although it may be coupled to the holding chamber 23 or MDI. The VHC is shaken before use, with the energy harvester device 80 actuating the linear generator 80, or a piezo element, so as to harvest or collect some of the kinetic energy created by the shaking and transform it into usable electrical energy. The generator generates energy stored in an energy storage device, such as a battery 230.

The energy harvesting device 80 may also be located inside the VHC, for example in a cavity 88 of the user interface 26, or in the interior cavity 24. When the device 80 is shaken, electrical energy is generated. Potential energy available may be up to 1 mW.

The energy harvester system 80 may be incorporated into a VHC to generate electricity through the user's movement. The generator may reduce or eliminate how often the user would have to charge their device. It also provides an output and feedback information on how the patient is using the device.

Dose Counter Shaking

Figure 10A:
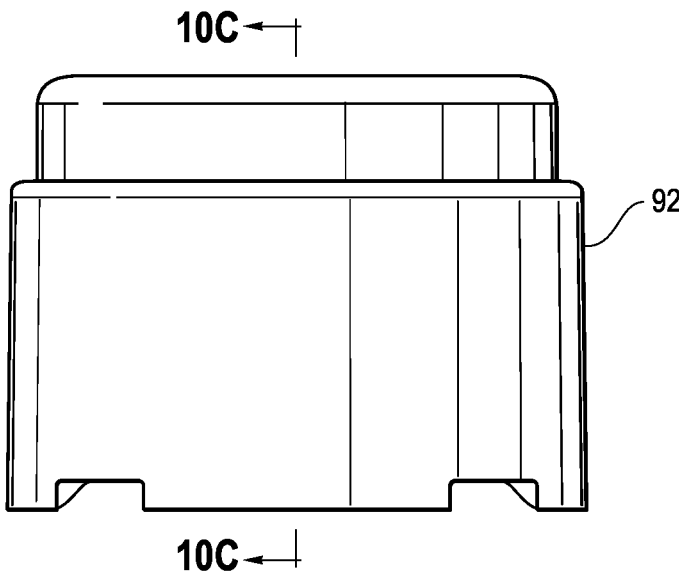
FIGS. 10A and B show a side and cross-sectional view of an MDI dose counter with a shaking energy harvester device and system.
Figure 10B:
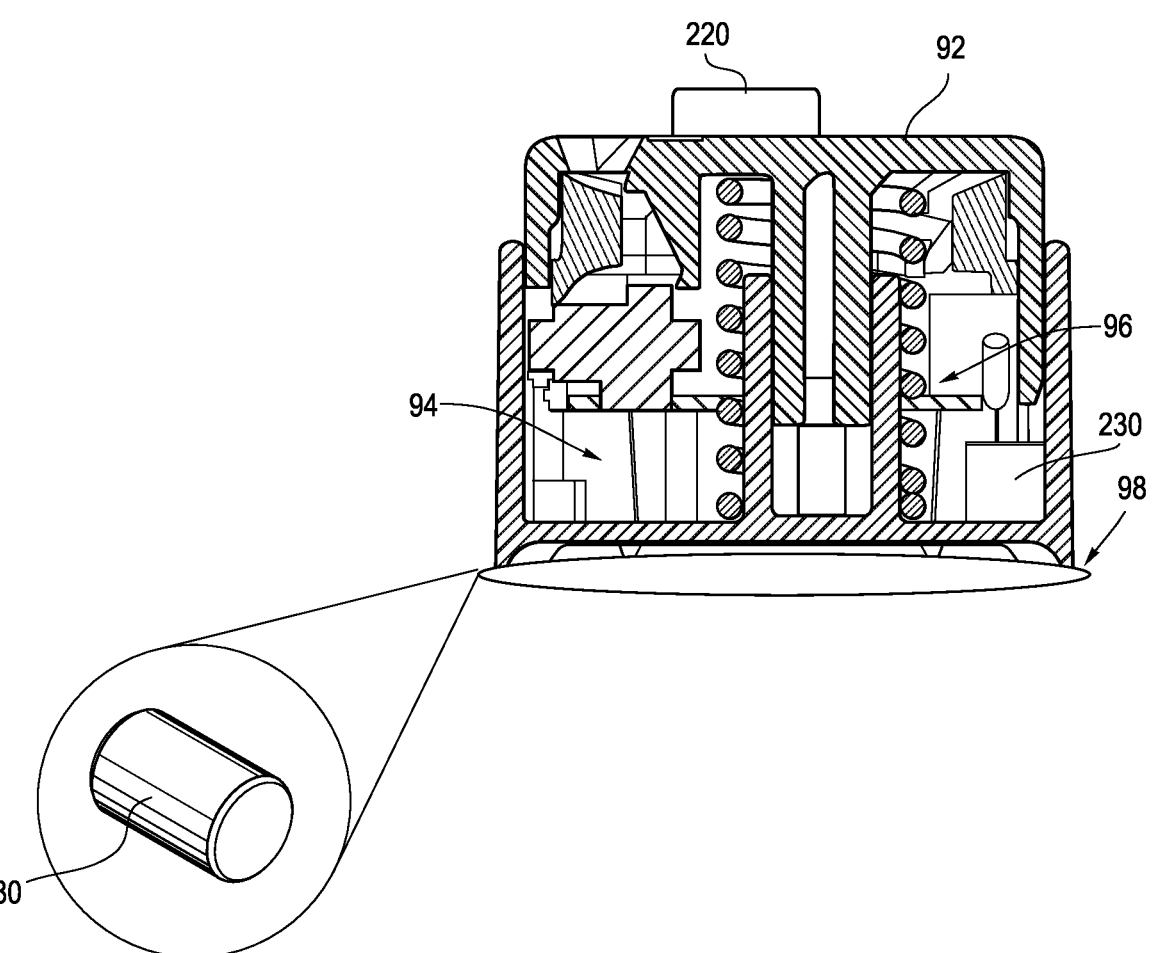

Referring to FIGS. 10A and B, an energy harvesting device 80 may incorporate a piezo element or linear generator to transform the energy from shaking the MDI and/or dose counter 92 connected thereto before use into electrical energy.

A dose counter 92 containing an energy harvester 80 within cavity 94, 96 or 98. When shaken before use the energy harvester 80 will generate usable electrical energy. Potential energy available may be up to 1 mW.

The energy harvester 80 may be incorporated into the dose counter 92 to generate electricity through user's movement, for example shaking the MDI that includes or incorporates a dose counter. The energy harvester may also be disposed or secured to other parts of the MDI, for example in the actuator boot, or to the outside thereof. The harvester or generator may reduce or eliminate how often the user would have to charge their device. The generator generates energy stored in an energy storage device, such as a battery 230. The system may also provide feedback information on how the patient is using the device.

TMAI Clicking Energy Harvesting

Figure 11A:
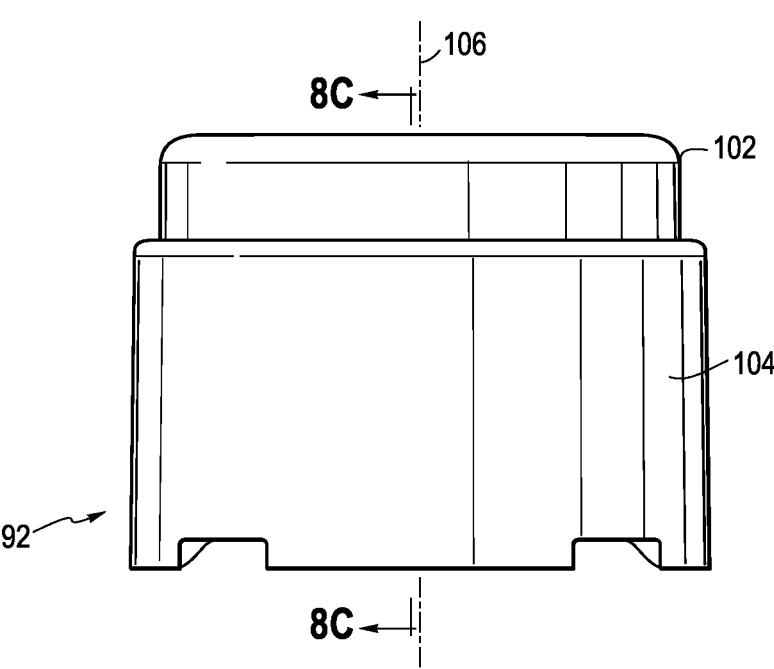
FIGS. 11A and B show side and cross-sectional views of an MDI dose counter with an actuator energy harvester device and system.
Figure 11B:
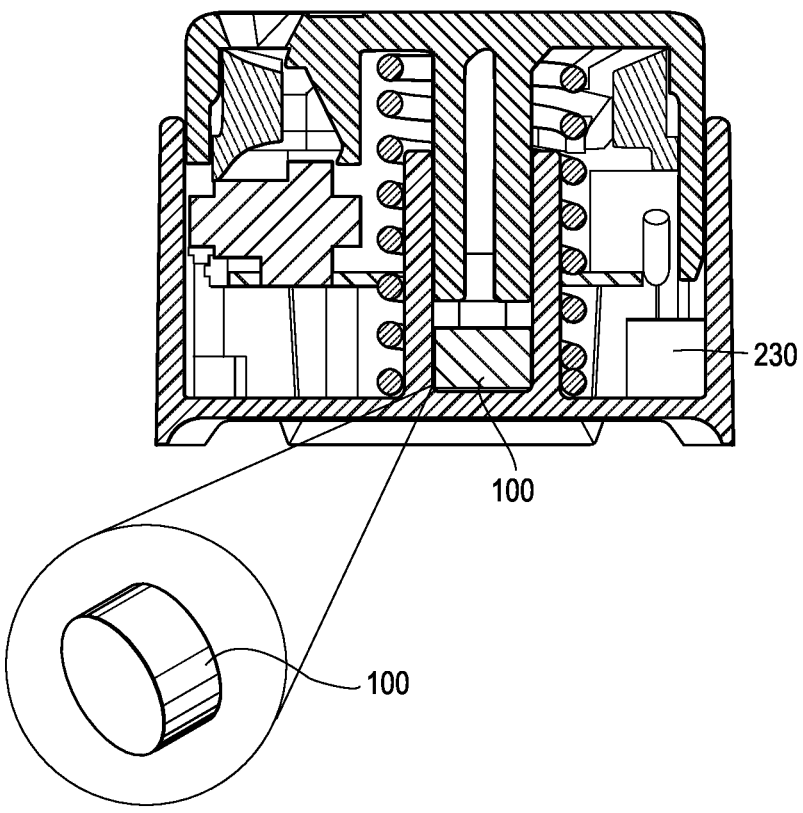

FIGS. 11A and B show an energy harvesting device 100 using a piezo element or linear generator to transform the energy from clicking the dose counter 92, for example by moving one housing component relative to another along a longitudinal axis 106 or moving a component of the MDI 130 relative to another along the axis 106, into electrical energy.

A dose counter 92 or MDI 130 may incorporate an energy harvester device or system 100. When the device, e.g., dose counter 92 or MDI 130, is actuated (e.g., clicked) the piezo element 100 is compressed generating usable electrical energy. The system generates energy stored in an energy storage device, such as a battery 230. Potential energy available may be up to 360 mW.

Incorporating an energy harvester device 100 into a dose counter 92 or MDI 130 may generate electricity through the patient's regular use of the device. This generator or harvester may reduce or eliminate how often the user would have to charge their device. It also provide an output or feedback information on how many times the user has used the device.

Energy Harvesting Through Solar Sleeve

Figure 12A:
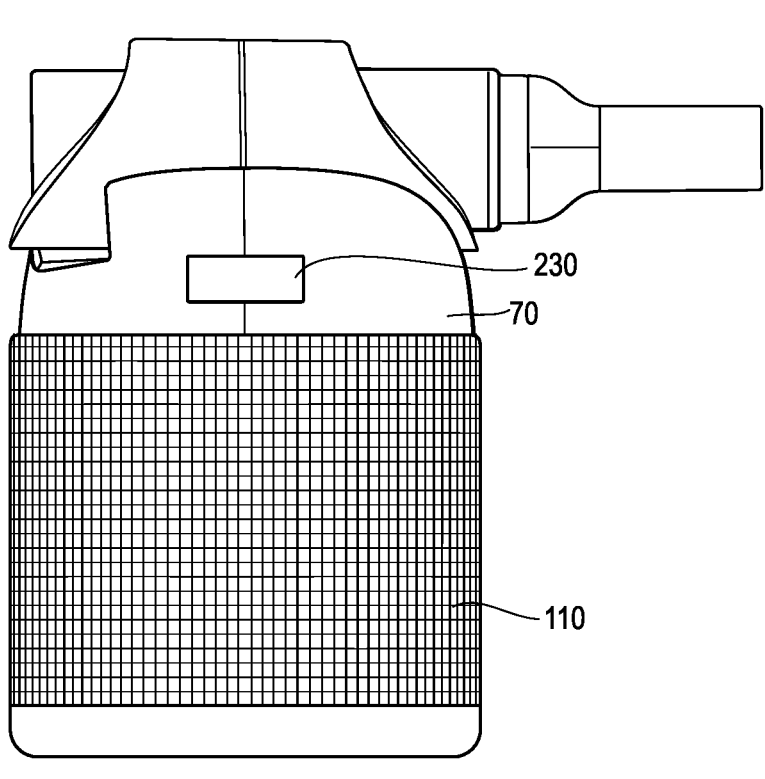
FIGS. 12A and B show an OPEP solar energy harvester device.
Figure 12B:
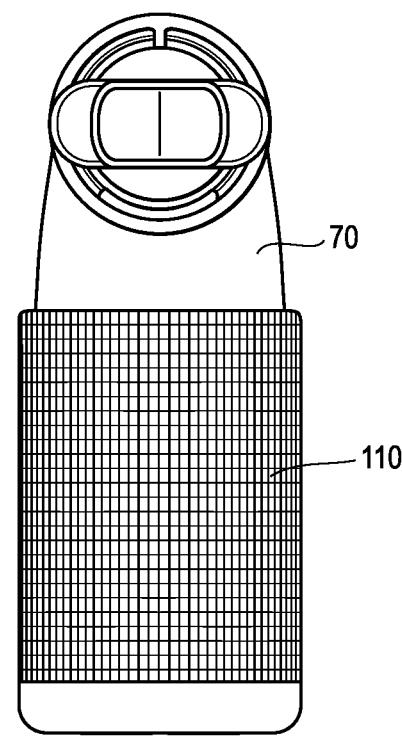

Referring to FIGS. 12A and B, an energy harvesting device or system may include a component such as a custom sized solar panel sleeve 110 dimensioned and shaped to fit over select medical devices, such as an OPEP device 70.

OPEP Solar Sleeve

Referring to FIGS. 12A and B, a removable solar sleeve 110 for the OPEP device is shown.

The solar sleeve 110 is shaped to fit over the OPEP device. When put on, the sleeve will automatically connect and begin transferring electrical energy if exposed to light. The sleeve generates energy stored in an energy storage device, such as a battery 230.

By incorporating an energy harvester onto an OPEP device to generate electricity through solar energy, the sleeve 110 may reduce or eliminate how often the user would have to charge their device.

VHC Solar Sleeve

Figure 13A:
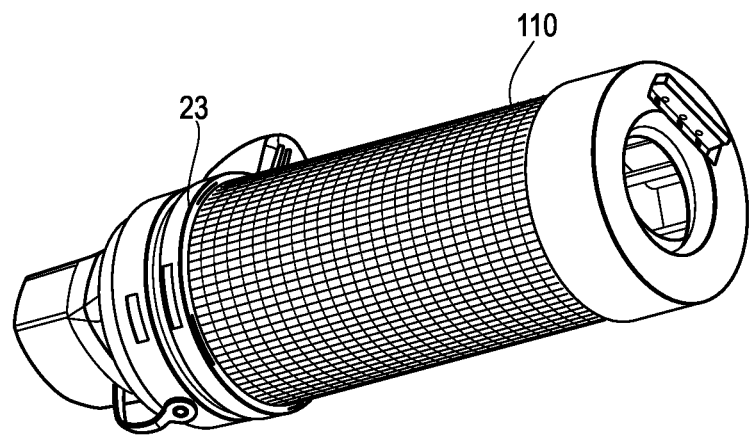
FIGS. 13A and B show a VHC solar energy harvester.
Figure 13B:
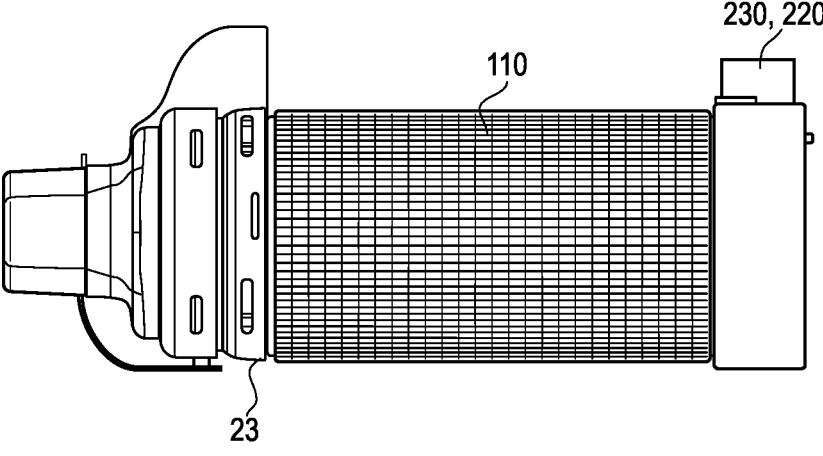

Referring to FIGS. 13A and B, a removable solar sleeve 110 for a VHC device is shown.

The solar sleeve 110 is dimensioned and shaped to fit over the VHC device, for example by partially or wholly surrounding the holding chamber 23. When "on," the sleeve 110 will automatically connect and begin transferring electrical energy if exposed to light. The sleeve generates energy stored in an energy storage device, such as a battery 230.

Incorporating an energy harvester device 110 onto a VHC device to generate electricity through solar. This sleeve 110 would reduce or eliminate how often the user would have to charge their device.

NEB Pump Solar Energy Harvesting

Figure 14A:
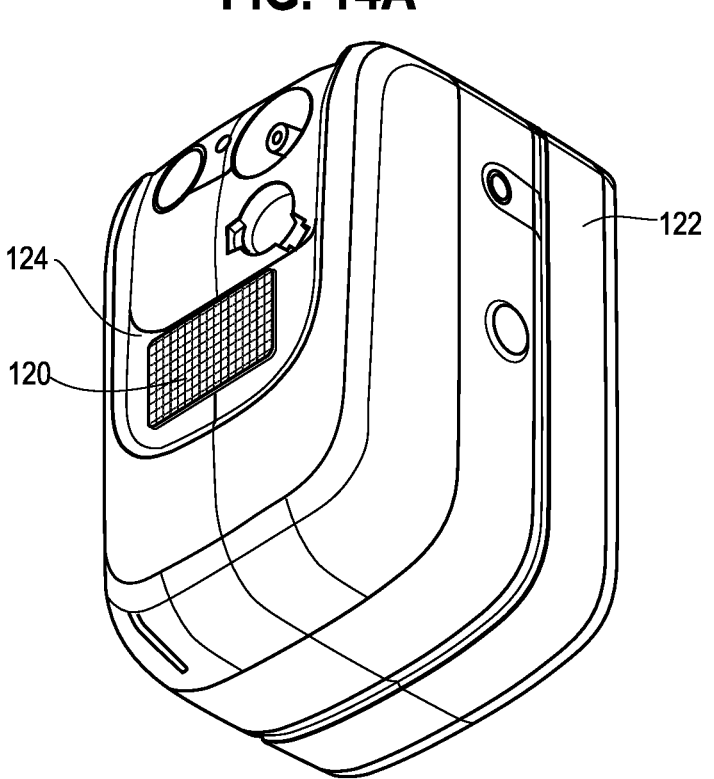
FIGS. 14A and B show a portable compressor with a solar energy harvester.
Figure 14B:
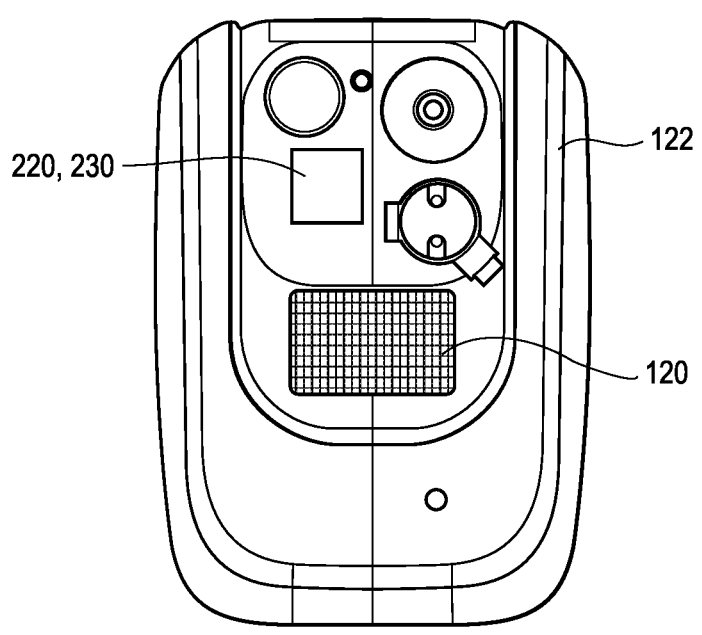

Referring to FIGS. 14A and B, an energy harvesting component is configured as a solar cell/unit 120, or panel, coupled to or integrated into a portable nebulizer pump 122.

The solar cell/unit 120 is located on top of a compressor 124 to charge the battery in one embodiment. The solar unit generates energy stored in an energy storage device, such as a battery 230.

An extended duration of use can be achieved before needing to charge the device with a wall outlet allowing for the user to take it to more remote locations with less worry of the battery dying.

Energy Harvesting with Peltier

Figure 15A:
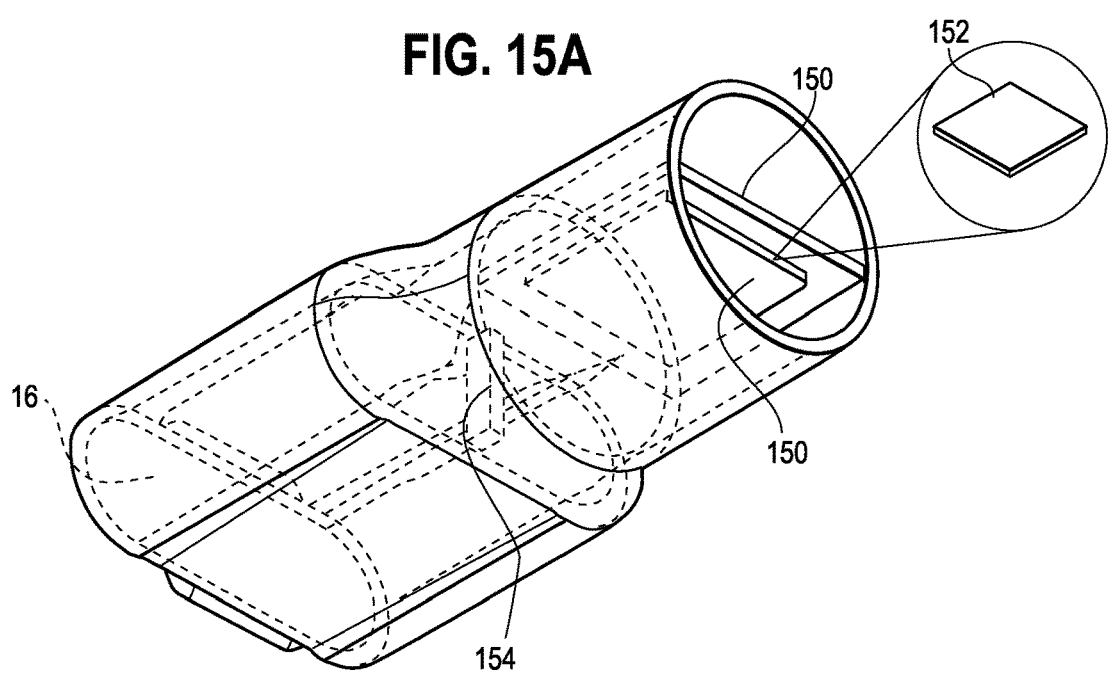
FIGS. 15A-C show perspective, side and end views of a temperature differential energy harvester.
Figure 15B:
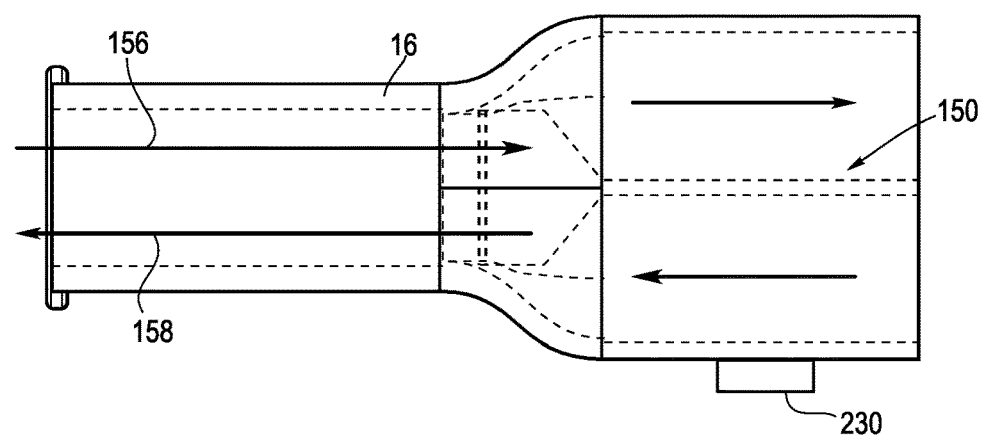
Figure 15C:
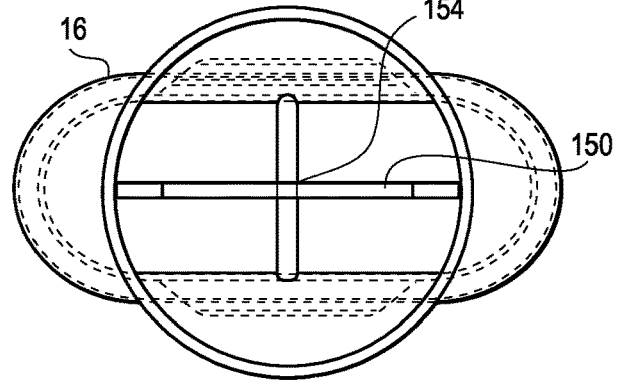

Referring to FIGS. 15A-C, an energy harvester device or system 150 incorporates a peltier 152 to generate electrical energy through the temperature difference within a device, or on opposite sides of the peltier.

OPEP Mouthpiece Temperature Differential Energy Harvesting

Referring to FIGS. 15A-C, the energy harvesting device or system 150 that uses the temperature difference between exhaled air 156 and inhaled air 158 to generate electrical energy is shown.

The energy harvesting device 150 includes a Peltier element 152 inside of user interface, shown in one embodiment as a mouthpiece 16. A split valve 154 directs air flow along the two paths 156, 158. The temperature difference, with the exhalation air 156 being warmer, between the two air flows 156, 158 heats up one side of the Peltier 152 relative to the other generating electrical energy. The system generates energy stored in an energy storage device, such as a battery 230.

Integrating a peltier element 152 into the mouthpiece 16, for example an OPEP device, or any other medical device such as a VHC, dry powder inhaler, and/or nebulizer. The energy harvester would reduce or eliminate how often the user would have to charge their device. It also provides feedback information on how the patient is using the device.

NEB Pump Temperature Differential Energy Harvesting

Figures 16A, 16B, 16C:
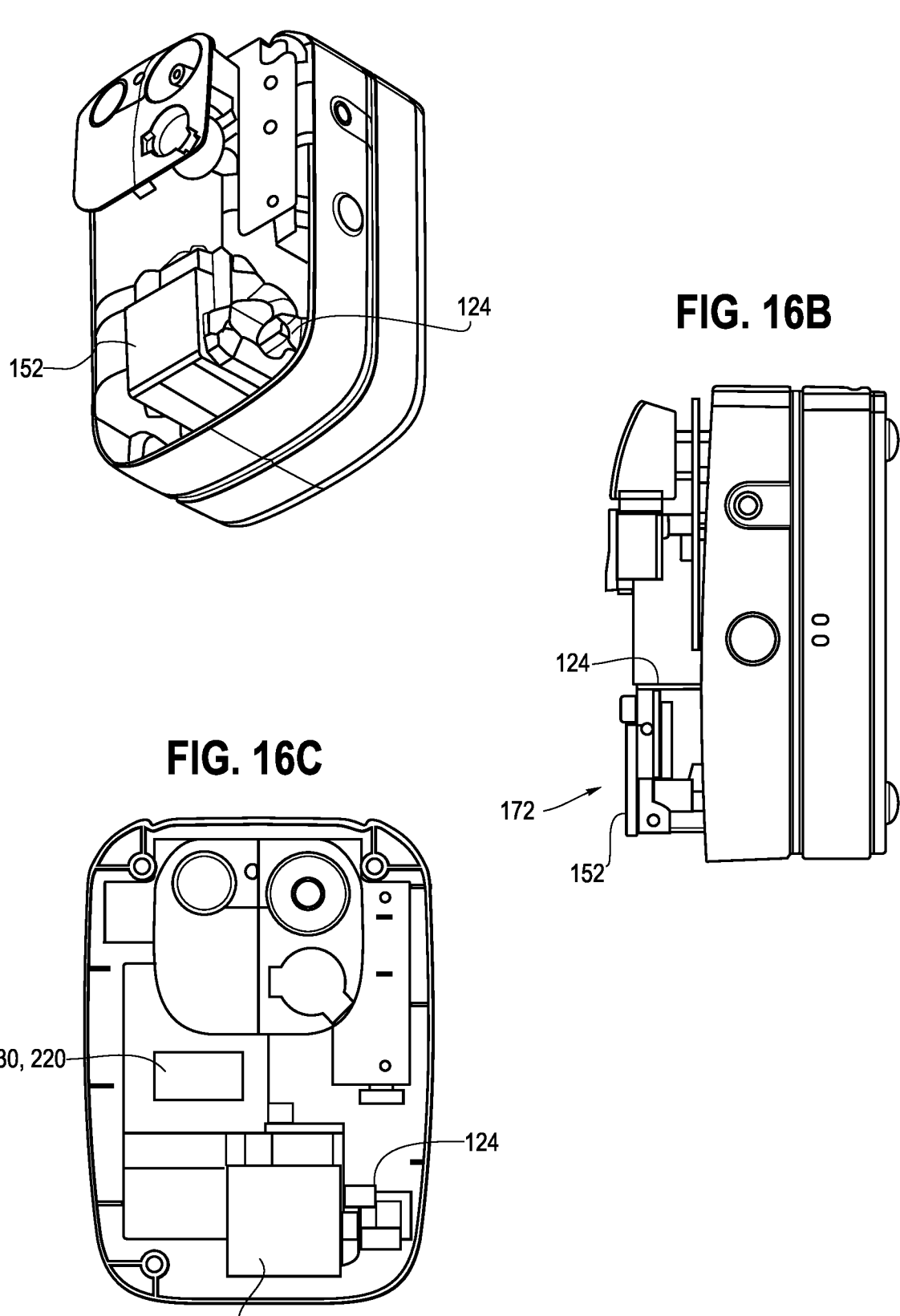
FIGS. 16A-C show perspective, side and end views of a portable compressor temperature differential energy harvester device.

Referring to FIGS. 16A-C, an energy harvester 170 includes a peltier device or element 152 to recycle back wasted heat energy on a portable compressor 124.

The peltier device 152 is located between the compressor 124 and ambient air 172. When the compressor 124 runs and heats up, the compressor creates a temperature differential between the pump and the ambient air 172. This heats up one side of the peltier element more than the other, which generates electrical energy. The system generates energy stored in an energy storage device, such as a battery 230. Integrating the peltier element 152 onto the pump or compressor 124 may reduce how often the user would have to charge their device. It also provides feedback information about how hot the pump is getting.

Piezo Membrane Energy Harvesting

Figures 17, 18A, 18B:
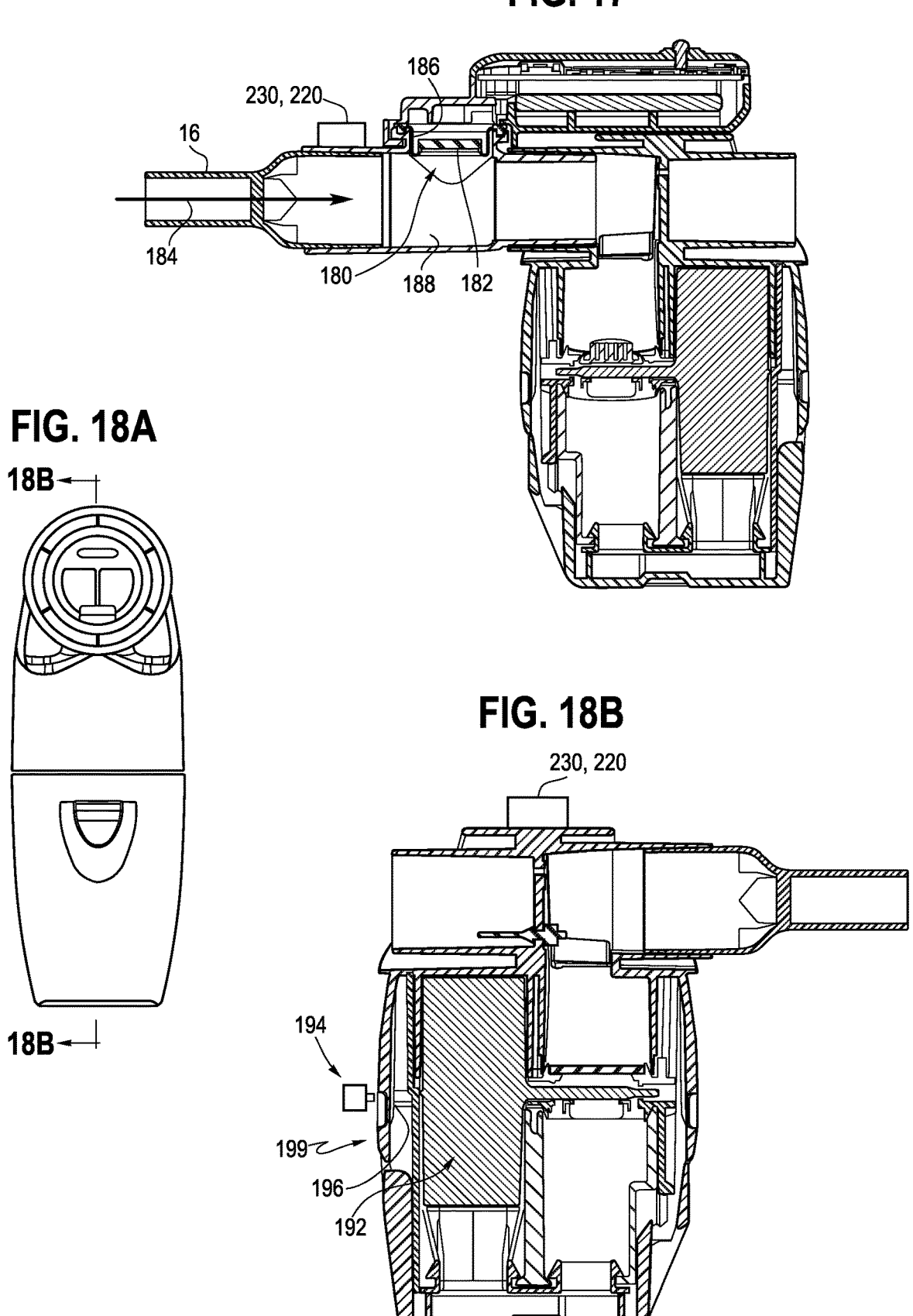
FIG. 17 shows a cross-section of an OPEP device having a piezo membrane energy harvester.
FIGS. 18A and B show side and cross-sectional views of an OPEP energy harvester device.

Referring to FIG. 17, an energy harvester device 180 includes a piezo element 182 attached to a flexible membrane 186 on an OPEP device.

The flexible membrane 186 with the piezo element 182 attached is coupled to a mouthpiece 16, for example on an OPEP. When air flow in the direction 184 during exhalation, an oscillating pressure is created within a cavity 188 adjacent the membrane 186. The oscillating pressure causes the membrane 186 to vibrate or oscillate, thereby deforming the piezo element 182, which creates electrical energy. The system generates energy stored in an energy storage device, such as a battery 230. Potential energy available may be up to 8 mW.

Integrating the piezo element 162 into the mouthpiece 16 of an OPEP device may reduce or eliminate how often the user would have to charge their device. It also provides feedback information on how the patient is using the device.

OPEP Oscillating Vane Energy Harvesting

Referring to FIGS. 18A and B, an energy harvesting device 190 uses the moving components within the OPEP to generate electrical energy is shown.

When the OPEP is in use, a vane component 192(2) moves back and forth. A rotation generator 194 may be coupled to the shaft 196 of the vane 192. The oscillation of the vane 192 rotates the shaft and drives the generator 194 to generate usable electrical energy. The system generates energy stored in an energy storage device, such as a battery 230. Potential energy available may be up to 8 mW.

Integrating a generator 194 into an OPEP device may reduce or eliminate how often the user would have to charge their device. It also provides feedback information on how the patient is using the device.

Magnetic Ball Energy Harvesting

Figure 19:
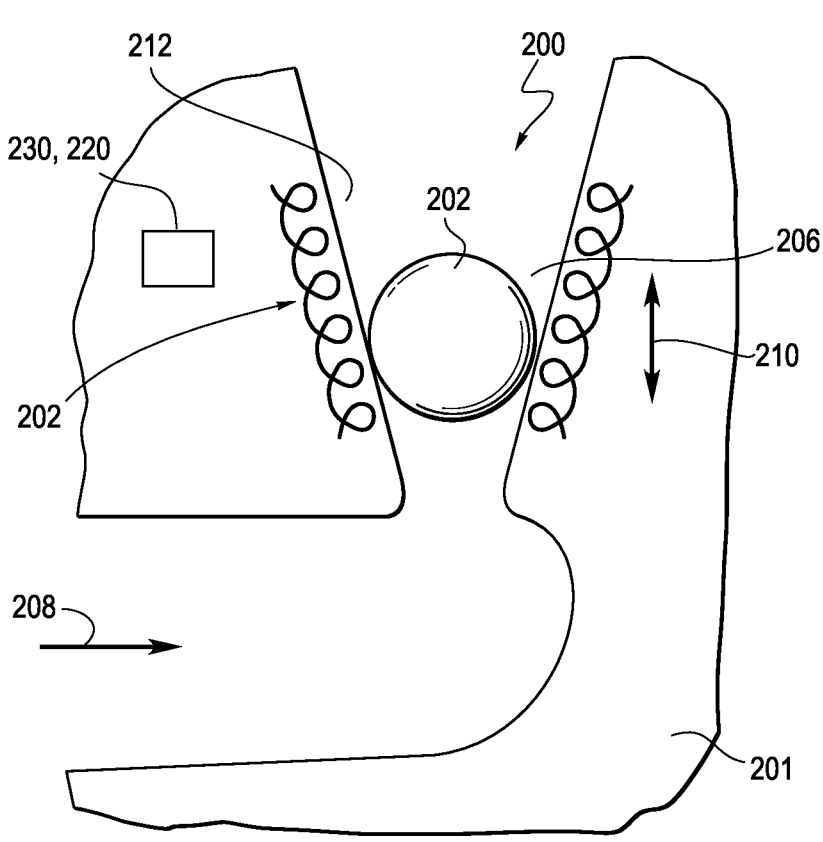
FIG. 19 shows an oscillating pressure magnetic ball energy harvester device.

Referring to FIG. 19, an energy harvesting device 200 uses oscillating air pressure to generate electrical energy.

An energy harvesting device includes a housing 201 with a magnetic ball 202 disposed inside of a copper coil 204. When airflow passes through a passageway 206 in a first direction 208 the magnetic ball 202 will move up and down within a channel 212, which may be tapered, along axis 210. This movement, or oscillation of the magnetic ball 202 within the copper coil 202 and channel 212 will generate usable electrical energy. The system generates energy stored in an energy storage device, such as a battery 230.

Figure 20:
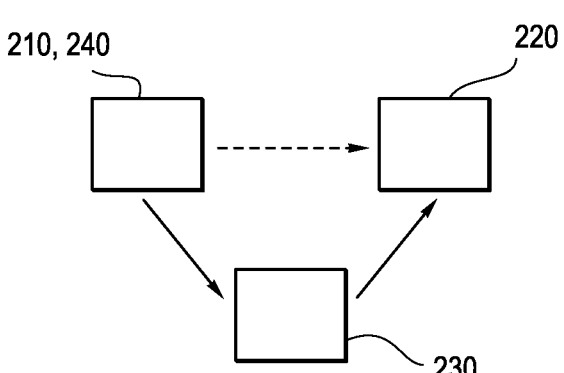
FIG. 20 is a schematic diagram of the energy harvesting system.

The "3945K2" Spherical Neodymium magnet from McMaster-Carr may be used in this embodiment Energy Use Referring to FIG. 20, the energy harvesting devices and systems 210 disclosed herein provide energy depleting components, or outputs 220. Exemplary energy intensive/using components, or outputs 220, include without limitation a microcontroller, sensor, a communication protocol and/or transmitter. Estimated energy used by these components is listed below (Table 1). The medical device includes a user interface component, with an energy harvesting system coupled to the user interface component. The energy harvesting system includes an energy harvesting component 240, disclosed above, operable to generate electrical energy in response to interfacing with the user interface component. The power storage device 230 is connected to the energy harvesting component and is operable to store the electrical energy received from the energy harvesting component 240. In one embodiment, the power storage device or component is a battery, capacitor (e.g., super capacitor), or other suitable device. The output 220 is coupled to the user interface and is operably connected to the power storage device 230.

TABLE 1

| Estimated Energy use based off of; Microcontroller - ATSAML22G18A-UUT, Bluetooth LTE - ATBTLC1000A- MU-T, Sensor - ZPA2326-0311A-R | | |
|---|---|---|
| Part | Standby Energy [uW] | Active Energy [mW] |
| Microcontroller | 0.66 | 0.94 |
| Bluetooth LTE | 6.6 | 10 |
| Sensor | 0.12 | 0.01 |
| total | 7.38 | 10.95 |

In operation, the user 300 interfaces with a user interface component, such as a holding chamber, OPEP, MDI or other medical device including for example and without limitation a mask or mouthpiece, with the harvesting energy system being coupled to the user interface component directly or indirectly, for example by attachment to the holding chamber or by being disposed in the holding chamber, OPEP or other medical device. Electrical energy is generated by the energy harvesting system, and an energy harvesting component in particular, in response to the user interfacing with the user interface component, for example by inhaling or exhaling into and through the user interface component, by shaking or actuating the user interface component, by exposing the user interface component to solar energy, by operating a pump or compressor and/or combinations thereof. The electrical energy is stored in a power storage device connected to the energy harvesting component. The power storage device may provide electrical energy to an output coupled, directly or indirectly, to the user interface. In various embodiments, the output may include one or more of a controller, sensor and/or communication protocol, such as a transmitter.

In various embodiments, the user interface includes one or more of a valved holding chamber, oscillating positive expiratory pressure device, pressurized metered dose inhaler (MDI), MDI dose counter, respiratory therapy device, dry powder inhaler, and/or nebulizer. The energy harvesting component may include one or more of a propeller, linear generator, piezo element, pressure differential harvester, shaking energy harvester, solar panel/unit/sleeve, peltier element, and/or rotary generator. In this way, it should be understood that the energy harvesting system may include more than one energy harvesting component, and/or more than one type of energy harvesting component. In one embodiment, the power storage device includes a battery and/or capacitor. The step of interfacing with the user interface component may include one or more of inhaling from and/or exhaling into the user interface component, shaking/moving the user interface component, actuating the user interface component, positioning the user interface component to receive solar energy, and/or operating a pump or compressor coupled to the user interface component.

Although the present invention has been described with reference to preferred embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

What is claimed is:

1. A dose counter for use with a metered dose inhaler, the dose counter comprising:
   a housing configured to be attached to the metered dose inhaler;
   a single energy harvesting component disposed in and moveable relative to the housing, the single energy harvesting component being configured to generate electrical energy in response to movement of the single energy harvesting component relative to the housing both (i) during actuation of the metered dose inhaler and (ii) in the absence of actuation of the metered dose inhaler; and
   a power storage device connected to the energy harvesting component and operable to store the electrical energy received from the energy harvesting component.

2. The dose counter of claim 1 further comprising an output operably connected to the power storage device, wherein the output comprises one or more of a controller, sensor and/or communication protocol.

3. The dose counter of claim 1 wherein the single energy harvesting component comprises a piezo element.

4. The dose counter of claim 3, wherein the single energy harvesting component comprises a mass suspended on the piezo element.

5. The dose counter of claim 1 wherein the single energy harvesting component comprises a linear generator.

6. The dose counter of claim 5 the linear generator comprises a magnet moveably disposed in a coil.

7. The dose counter of claim 1 wherein the power storage device comprises a battery.

8. The dose counter of claim 1 wherein the housing comprises a first housing component moveable relative to a second housing component along a longitudinal axis, wherein the single energy harvesting component is configured to generate electrical energy in response to the movement of the first housing component relative to the second housing component.

9. The dose counter of claim 8 wherein the single energy harvesting component comprises a piezo element, wherein the first housing component deforms the piezo element.

10. The dose counter of claim 8 wherein the single energy harvesting component comprises a linear generator responsive to the relative movement of the first and second housing components.

11. The dose counter of claim 1, wherein the single energy harvesting component is movable relative to the housing in response to a pressure differential.

12. The dose counter of claim 1, wherein the single energy harvesting component is movable relative to the housing in response to shaking of the housing.

13. The dose counter of claim 1, wherein the dose counter is a top-mounted actuation indicator.

14. A method of using a dose counter comprising:
   moving a dose counter housing coupled to a metered dose inhaler;
   moving a single energy harvesting component disposed in the housing in response to moving the dose counter housing, without actuating the metered dose inhaler;
   harvesting energy with the same single energy harvesting component in response to the movement of the same single energy harvesting component, both with and without actuating the metered dose inhaler; and
   storing the electrical energy in a power storage device disposed in the housing and connected to the energy harvesting component.

15. The method of claim 14 wherein moving the dose counter housing comprises moving a first housing component relative to a second housing component, and wherein moving the single energy harvesting component comprises moving the single energy harvesting component with the first housing component.

16. The method of claim 15 wherein the single energy harvesting component comprises a piezo element, and wherein moving the single energy harvesting component with the first housing component comprises deforming the piezo element with the first housing component.

17. The method of claim 15 wherein the single energy harvesting component comprises a linear generator.

18. The method of claim 14, wherein moving the single energy harvesting component is performed before actuating the metered dose inhaler.

19. The method of claim 14, wherein moving the single energy harvesting component comprises shaking the dose counter housing.

20. The method of claim 14, wherein moving the single energy harvesting component comprises vibrating the energy harvesting component.

* * * * *